United States Patent
Kröning et al.

(10) Patent No.: US 8,365,600 B2
(45) Date of Patent: Feb. 5, 2013

(54) METHOD USING ULTRASOUND FOR THE NON-DESTRUCTIVE EXAMINATION OF A TEST BODY

(75) Inventors: Michael Kröning, Saarbrücken (DE); Dieter Hentschel, Dresden (DE); Ludwig von Bernus, Windsbach (DE); Andrey Bulavinov, Saarbrücken (DE); Krishna Reddy, Saarbrücken (DE)

(73) Assignee: Fraunhofer-Gesellschaft zur Förderung der Angewandten Forschung e.V., Munich (DE)

( * ) Notice: Subject to any disclaimer, the term of this patent is extended or adjusted under 35 U.S.C. 154(b) by 970 days.

(21) Appl. No.: 11/721,235

(22) PCT Filed: Dec. 9, 2005

(86) PCT No.: PCT/EP2005/013237
§ 371 (c)(1),
(2), (4) Date: Oct. 13, 2009

(87) PCT Pub. No.: WO2006/061240
PCT Pub. Date: Jun. 15, 2006

(65) Prior Publication Data
US 2012/0036934 A1 Feb. 16, 2012

(30) Foreign Application Priority Data
Dec. 11, 2004 (DE) .......................... 10 2004 059 856

(51) Int. Cl.
*G01N 29/06* (2006.01)

(52) U.S. Cl. ............................................ 73/602; 73/626
(58) Field of Classification Search .................... 73/622, 73/602, 625, 626, 628
See application file for complete search history.

(56) References Cited

U.S. PATENT DOCUMENTS

| | | | | |
|---|---|---|---|---|
| 4,275,598 A | * | 6/1981 | Engl | 73/622 |
| 4,699,007 A | * | 10/1987 | Kawashima et al. | 73/622 |
| 5,097,709 A | | 3/1992 | Masuzawa et al. | |
| 5,165,280 A | * | 11/1992 | Sternberg et al. | 73/622 |
| 6,048,315 A | * | 4/2000 | Chiao et al. | 600/447 |
| 2004/0093949 A1 | * | 5/2004 | Alleyne | 73/625 |
| 2004/0187582 A1 | | 9/2004 | Satoh | |
| 2004/0267135 A1 | * | 12/2004 | Takeuchi | 600/459 |

* cited by examiner

*Primary Examiner* — Peter Macchiarolo
*Assistant Examiner* — Rose M Miller
(74) *Attorney, Agent, or Firm* — Antonelli, Terry, Stout & Kraus, LLP.

(57) ABSTRACT

The invention is a method using ultrasound for non-destructive examination of a test body, whereby ultrasonic waves are coupled into the test body with one ultrasonic transducer or a multiplicity of ultrasonic transducers and the ultrasonic waves reflected inside the test body are received by a multiplicity of ultrasonic transducers and converted into ultrasonic signals. The ultrasonic signals detected in the single measurement periods are individually stored and are accessible for off-line evaluation after termination of the measurements. Application of corresponding reconstruction algorithms permits subsequent synthetization of any desired ultrasonic coupling-in angles and focussing into the volume region of the test body from the stored ultrasonic signals without requiring any additional ultrasonic measurements.

10 Claims, 1 Drawing Sheet

METHOD USING ULTRASOUND FOR THE NON-DESTRUCTIVE EXAMINATION OF A TEST BODY

BACKGROUND OF THE INVENTION

1. Field of the Invention

The present invention relates to a method using ultrasound for non-destructive examination of a test body, whereby ultrasonic waves are coupled into the test body with one or a multiplicity of ultrasonic transducers and the ultrasonic waves reflected inside the test body are received by a multiplicity of ultrasonic transducers and converted into ultrasonic signals, which form the basis of the non-destructive examination.

2. Description of the Prior Art

The method of using ultrasound for non-destructive examination of a test body, for example for the purpose of examining material for flaws, such as cracks, occlusions or other inhomogeneities, comprises coupling ultrasonic waves into the test body, detection of the ultrasonic waves transmitted or reflected through the test body, deflected, scattered and/or broken in the test body as well as the evaluation of the ultrasonic waves converted into ultrasonic signals.

The preceding state-of-the-art method of examination permits determining and evaluating the ultrasonic transmission and ultrasonic reflection properties of a test body. In this method, which originates from medical technology (ultrasonic diagnostics), imperfections inside the test body, such as cracks, foreign occlusions or boundaries in the material are imaged by means of corresponding evaluation of the received ultrasonic signals as regions with altered reflection properties. Position, shape and size of the imperfections can be represented three-dimensionally in a spatially high-resolution manner.

It is obvious that the fields of application of this method are substantial and diverse, for example, the application of the method for examining and detecting the homogeneity or solidity properties of structural components (concrete walls, ceiling elements or wall elements, etc.) or for examining for cracks, for instance in railroad car wheels or aircraft parts.

Suited in an advantageous manner for coupling in, receiving and detecting ultrasonic waves are piezoelectric ultrasonic transducers which are able to convert electrical energy into elastic mechanical energy and inversely.

Piezoelectric ultrasonic transducers are distinguished, in particular, by their linear behavior during conversion of elastic mechanical energy into electrical energy and inversely. Moreover, depending on size and shape, piezoelectric ultrasonic transducers have an aperture, that is a specific emission characteristic which determines the spatial coupling-in behavior of the ultrasonic waves inside the test body. If a multiplicity of single ultrasonic transducers are employed, the coupling-in area of the single ultrasonic transducers can be assembled directly adjacent to each other on the test body in such a manner that the result is an overall aperture defined cumulatively by the apertures of the single ultrasonic transducers. In order to couple in, for example, ultrasonic waves with largely the same amplitudes in a half-space inside the test body volume, it is necessary to select ultrasonic transducers with an emission characteristic which is ball-shaped to the extent possible. If, however, the ultrasonic transmission of ultrasonic waves into a test body at as small as possible propagation angle is desired, it is necessary to select an ultrasonic transducer with as great as possible a "directional characteristic".

In many applications using ultrasound for non-destructive material examination, a multiplicity of ultrasonic transducers are employed which are assembled in a so-called ultrasonic probe, or transducer for easier handling. Basically, it is necessary to differentiate between two types of transducers. If the transducer couples an ultrasonic wave package into the test body and the ultrasonic waves reflected inside the test body are received again, they are called impulse-echo probes. On the other hand, probes with separate ultrasonic transducers for coupling in the sound waves and receiving them again are referred to as transmission, and reception, probes.

In all prior art ultrasonic probes, the single ultrasonic transducers are each connected to a control device which is provided with separate control electronics for each ultrasonic transducer, that is each ultrasonic transducer has its own electrical control channel, in such a manner that single ultrasonic transducers can be activated separately and, for example, serve as an ultrasonic transmitter or an ultrasonic receiver. In particular, such type separate activation permits operating individual ultrasonic transducers, each with a different phase position and amplitude.

In order to conduct a measurement of the ultrasonic transmission capacity of a probe, the control device activates at least one of the ultrasonic transducers and usually a plurality of ultrasonic transducers, for a limited, brief interval to couple ultrasonic waves into the probe. The generated, coupled-in ultrasonic waves are, for example, reflected at imperfections inside the test body and are reflected as ultrasonic waves which return to the ultrasonic transducers. The ultrasonic transducers now operate as receivers of the ultrasonic waves which are converted into ultrasonic signals and are transmitted to the control device for evaluation. The interval between transmission and reception of the ultrasonic signals is usually referred to as a measurement period. For better signal detection and evaluation, a multiplicity of such measurement periods are conducted consecutively in order to obtain a tolerable signal-to-noise ratio.

Many applications call for as finely spatially resolved as possible determining the ultrasonic transmission properties and reflection properties of a test body inside the test body volume. To do so, a multiplicity of measurement periods are conducted in which the ultrasonic waves coupled into the test body are focussed onto a narrowly defined volume region, which is referred to as a "voxel".

As a result of focusing the elastic energy of the ultrasonic waves on a certain volume region inside the test body, the elastic energy reflected from this volume region in the form of reflected ultrasonic waves is significantly larger than if the ultrasonic coupling-in is not focussed. Focussing enhances measurement sensitivity.

The "phased-array" method is used to focus the ultrasonic waves in a certain volume region inside the test body. The ultrasonic transducers are arranged in an array on the surface of the test body and are activated in a phase-shifted manner to the transmission of the ultrasonic waves, that is time staggered to the ultrasonic transmission. By means of suited selection of the time staggering, constructive overlapping of the coupled-in ultrasonic waves according to Huygen's principle occurs in a certain volume region. In order to achieve as optimum as possible constructive overlapping of the ultrasonic waves in the volume region, the individual ultrasonic transducers operating as ultrasonic transmitters must be activated with identical signal forms.

Apart from focusing ultrasonic waves onto a certain volume region inside the test body, it is also possible, by selection of the phase shift, to preset a uniform coupling-in direction of the ultrasonic waves for the activation of the arrayed ultrasonic transducers. In this manner, it is possible to couple pivotable ultrasonic fields into the test body.

Signal evaluation in the prior art phased-array method occurs in such a manner that the individual reflected ultrasonic signals received in one measurement period are summed cumulatively considered by taking into consideration the phase shift employed at the beginning of the measurement period during ultrasonic coupling-in. In this manner, a cumulative signal is formed after each single measurement period. Looking at all the cumulative signals together allows drawing conclusions about the ultrasonic transmission properties and reflection properties in the entire test body volume physically accessible for the material examination method.

A drawback in using the phased-array method for non-destructive material examination of a test body, however, is the amount of time and technical equipment required to examine a test body as completely as possible, since the point is to obtain sufficiently reliable measurement signals from all the volume regions for complete signal evaluation. For example, in one measurement period or a multiplicity of single measurement periods, it is only possible to obtain information about the reflection properties in only one volume region of the test body. Examination of the entire test body volume requires a very great number of measurements, each with different phase activation, making the entire material examination very time consuming.

Another disadvantage is that a preset ultrasonic coupling-in angle determines the probe aperture so that the aperture cannot be optimally selected for all ultrasonic coupling-in angles which yields poorer measurement resolution.

A further drawback of the phased-array method is that a transmission channel and a reception channel has to be provided for each ultrasonic transducer with corresponding activation electronics, which has to be connected to the respective ultrasonic transducer via separate electrical connections. As the presently used ultrasonic probes usually comprise 16 or more ultrasonic transducers, connection between the probe and the control device usually requires a thick, inflexible and consequently unwieldy cable.

SUMMARY OF THE INVENTION

The present invention is an inexpensive method using ultrasound for nondestructive material examination of a test body with which the volume of the test body can be completely examined and the spatial resolution as well as the sensitivity of the measurement are optimized compared to the state of the art. Moreover, the amount of time and technical devices required for material examination are reduced.

The method according to the invention uses an ultrasound for non-destructive examination of a test body, in which ultrasonic waves are coupled into the test body with one or a multiplicity of ultrasonic transducers and the ultrasonic waves reflected inside the test body are received by a multiplicity of ultrasonic transducers and converted into ultrasonic signals which ultimately form the basis of the non-destructive examination.

The method of the invention includes the following process steps:

In a first step, a number of n ultrasonic transducers are disposed on the surface of a test body. The ultrasonic transducers are preferably applied directly or by means of a suitable coupling means to the surface of the test body. The ultrasonic transducers can be placed on the surface of the test body in an unordered manner or in an ordered manner in the form of one-dimensional arrays (horizontally in a row), two-dimensional arrays (field-shaped) or three-dimensional arrays (based on the three-dimensional surface of the test body).

The n ultrasonic transducers are each suited in an advantageous manner to couple in and receive ultrasonic waves, that is the transducers are utilized, respectively as ultrasonic transmitters and as ultrasonic receivers. However, the transducers may be used singly as ultrasonic transmitters or as ultrasonic receivers, which, however, if spatial resolution of the measurement results is the same, requires a greater number of ultrasonic transducers to be used.

Preferably ultrasonic transducers are piezoelectric transducers. But transducers based on electromagnetic, optical or mechanical principles can also be employed.

In an advantageous manner, the n ultrasonic transducers are assembled in a manually easy to handle an ultrasonic probe permitting simple use and application to the test body surface. Other applications of the ultrasonic transducer, for example to the opposite surfaces of the test body, are obtained dependent on the shape and size of the test body and the respective object of examination. It has proven that the method according to the invention permits obtaining optimum spatial resolution of the measurement results if the number of provided ultrasonic transducers selected is at least 16.

In a second step, a first ultrasonic transducer or a first group of ultrasonic transducers is selected from the entire number of n ultrasonic transducers, whereby if a group of ultrasonic transducers is selected, the number i of the ultrasonic transducers of the group should be lower than the overall number n of all the ultrasonic transducers.

Setting i as the number of ultrasonic transmitters determines the elastic energy coupled into the test body per activation of the ultrasonic transmitters provided that the i ultrasonic transmitters are activated simultaneously. The larger the number of all the simultaneously activated transmitters that is selected, the greater the elastic energy that is coupled into the test body. Furthermore, setting i, if possible, is desired in such an advantageous manner that i directly adjacent ultrasonic transducers are selected as a continuous planar ultrasonic transmitter array. Furthermore, provided that all the transmitters transmit simultaneously, the i number of ultrasonic transmitters and the actual composition of the transmitter group, in particular their arrangement on the test body surface, determine the overall emission characteristic (aperture) of the transmitter group and, in addition, the sensitivity as well as resolution capacity of the measurements.

Furthermore, the first ultrasonic transducer, that is i=1, or all i ultrasonic transducers of the first group are activated to emit ultrasonic waves which couple into the test body. The ultrasonic waves are reflected at imperfections inside the test body or at the test body surfaces opposite the respective coupling-in regions and return to the surface region of the n ultrasonic transducers applied on the test body surface, in which all n or only a limited part m receives the ultrasonic waves. The number m should always be greater than the number i of the ultrasonic transducers which are ultrasonically transmitting.

Depending on each single measurement period, the m ultrasonic transducers functioning as ultrasonic receivers or maximally the ultrasonic waves received by all n ultrasonic transducers are converted into ultrasonic signals and stored, that are conveyed into a corresponding storage unit and stored there.

As an alternative to simultaneous activation of i selected ultrasonic transducers of one group acting as ultrasonic transmitters, phase-shifted activation is also feasible, that is partially or completely time staggering, of the ultrasonic transmitters. As described in the preceding in connection with the phased-array principle, the ultrasonic coupling-in direction, and focussing, of the elastic energy of the ultrasonic waves onto a certain volume region inside the test body can be carried out in this manner. The aperture of the i ultrasonic transmitters can be optimized and set to specific coupling-in directions or focussings.

Fundamentally, transmitter-specific modulation of the ultrasonic transducers acting as transmitters is not required, that is all the ultrasonic transmitters are activated identically. For the purpose of possible simplification or special evaluation of the measurement signals, it may be advantageous to allocate the received measurement signals to the corresponding ultrasonic transmitter. For this purpose the i ultrasonic transducers of a group are actively modulated, that is each single ultrasonic transducer is activated with a different modulation in such a manner that the ultrasonic waves coupled into the test body can be transmitter specifically detected.

After conducting one or a multiplicity of measurement periods, an altered selection of ultrasonic-wave-generating ultrasonic transmitters occurs. For better measurement sensitivity, it is advantageous to conduct several measurement periods with the same ultrasonic transmitter constellation in order to obtain a better signal-to-noise ratio by means of statistical signal evaluation. If in each case a single ultrasonic transducer acting as the ultrasonic transmitter, a different ultrasonic transmitter is selected for emitting ultrasonic waves. Preferably, an ultrasonic transducer is selected that lies directly adjacent to the ultrasonic transducer which is activated last. If a multiplicity of ultrasonic transducers are assembled to a group, another group of ultrasonic transducers has to be formed. Although its number i is identical, its composition should, however, differ from that of the previously selected composition at least by one ultrasonic transducer.

In this manner, it is possible to transmit ultrasonic waves from different coupling-in regions into the test body. Like in the first measurement period or in the first measurement cycle composed of a multiplicity of first measurement periods, with the new ultrasonic transmitter constellation reflected ultrasonic waves are also received with all n ultrasonic transducers or with a part m of the ultrasonic transducers and converted into ultrasonic signals, which also are ultimately stored. All n or m ultrasonic transducers functioning to receive ultrasonic waves remain unchanged despite the changed ultrasonic transmitter constellations to permit as simple as possible later measurement evaluation which is described in the following.

With the aforedescribed process steps of repeated activation of one further ultrasonic transducer or of a group of ultrasonic transducers with an altered composition of ultrasonic transducers, reception and storage of the obtained measurement signals are repeated as often as preset to determine in this manner the transmission capacity, and reflection capacity of the test body from a multiplicity and preferably from all, possible transmission positions.

For example if only one ultrasonic transducer, that is $i=1$ is activated as the ultrasonic transducer, maximally n measurement periods or n measurement cycles, each comprising a selectable number of measurement periods, can be conducted. If one group comprising i ultrasonic transducers is activated, maximally all i permutations of n ultrasonic transducers can be conducted.

As a result of conducting the preceding process steps, a multiplicity of the m measurement signals are stored per measurement period per measurement cycle, which should be analyzed in the following manner based on examination of a test body for a specific purpose. A special aspect is the possibility of evaluating the stored measurement signals later after the actual measurement of the test body. Evaluation of the ultrasonic signals occurs off-line using a reconstruction algorithm, which is selected based on a virtually preset coupling-in angle and/or virtual focussing of the ultrasonic waves coupled into the test body and is applied to the stored ultrasonic signals. With the aid of such reconstruction algorithms, synthetic three-dimensional images of the ultrasonic transmission properties, and reflection properties of the test body can be computed from the stored ultrasonic signals without requiring additional ultrasonic measurements. This reconstruction principle is based on the application of the synthetic aperture focussing technique (SAFT), comprising projecting of all received ultrasonic signals onto a common temporal axis. All of the ultrasonic signals reflected from a certain reflector can be added in phase. Later reconstruction of any coupling-in angle is obtained by a phase-shifted addition of the received signals from different ultrasonic receivers. Off-line evaluation permits synthetic reconstruction of practically any coupling-in angle and in this manner running an ultrasonic "sweep" through the data.

Compared to the known state of the art, the method of the invention provides a faster, inexpensive method permitting flexible off-line evaluation and assessment of the detected measurement data.

An advantageous further development of the method of the invention provides for analog/digital conversion in which the analog ultrasonic signals of the m ultrasonic receivers are converted into digital signals and conveyed serially to a storage unit in digital form.

In another advantageous embodiment, the electrical triggering and activation of all n ultrasonic transducers as digital data occurs between the control unit required for triggering and the ultrasonic transducers. The A/D and D/A converters are provided in the direct vicinity of each ultrasonic transducer. These electronic components can be accommodated directly on the ultrasonic transducers or in a corresponding ultrasonic probe, thereby permitting considerable reduction of the number and thickness of the hitherto used analog connection cables between the probe and the control unit. Furthermore, in this manner the method is performed with a smaller number and more compact devices.

BRIEF DESCRIPTION OF THE DRAWINGS

The present invention is described by way of example in the following, without the intention of limiting the scope or spirit of the invention, using preferred embodiments with reference to the accompanying drawings.

DESCRIPTION OF THE PREFERRED EMBODIMENTS

Figure 1A:
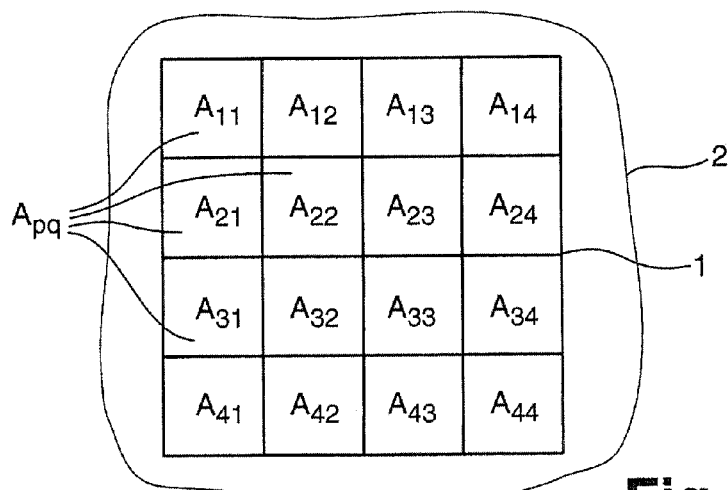
FIG. 1a shows an array of 4×4 ultrasonic transducers.

FIG. 1a shows a top schematical view of a 4×4 transducer array arrangement 1 with sixteen ($n=16$) ultrasonic transducers $A_{pq}$. The indices p and q provide the position of the ultrasonic transducer $A_{pq}$ in the array according to row and column. The transducer array 1 is placed on the surface of a test body 2. In this preferred embodiment, the number i of transmitters equals 1 ($i=1$) and the number m of receivers equals 16 (m=n=16) which are selected for all the to-be-conducted measurement periods.

Figure 1B:
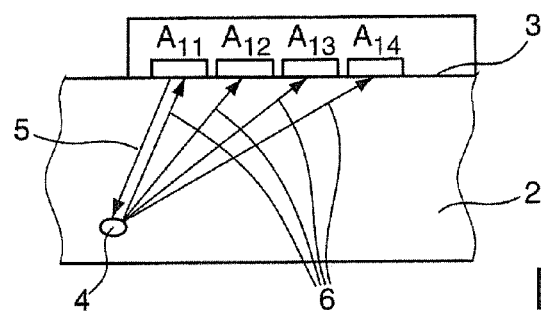
FIG. 1b shows a cross section of a probe and a schematic representation of the method for $i=1$, $n=m=4$.

FIG. 1b shows a cross section of a test body 2 with the cross section area oriented perpendicular to the surface of the test body and through the first row of the ultrasonic transducer array 1 placed on the surface 3. Disposed on surface 3 of the test body 2 are, therefore, the four ultrasonic transducers $A_{11}$, $A_{12}, A_{13}, A_{14}$, of array 1 and the other transducers $A_{21}$-$A_{44}$. It is assumed that an imperfection 4 is present in the test body 2.

In a first measurement period, the ultrasonic transducer $A_{11}$ is activated as a transmitter. Transducer $A_{11}$ transmits ultrasonic waves along path 5 which intersect the imperfection 4. The ultrasonic waves 5 are reflected by it and along reflection paths 6 which impinge on all the illustrated transducers $A_{11}$-$A_{14}$ and on the other transducers $A_{21}$-$A_{44}$ of the array 1 are received by the same.

In the first measurement period (k=1), an ultrasonic signal $U_{k=1,pq}$ is generated in each ultrasonic transducer $A_{pq}$ (p=1, ..., 4 and q=1, ..., 4). These 4×4=16 ultrasonic signals are stored singly and serially in a storage unit. In the next measurement period (k=2, not depicted) the ultrasonic transducer $A_{12}$ couples ultrasonic waves into the test body 2. The different transmission position changes the coupling-in angle, and the "illumination angle" of imperfection 4 and thus the reflection geometry inside the test body 2. Consequently, in the second measurement period altered ultrasonic signals $U_{k=2,pq}$ are received at all 16 ultrasonic transducers $A_{pq}$ and are subsequently stored in the storage unit. It is assumed that a maximum of 16 measurement periods are each conducted with a different transmitter constellation. Conducting all 16 measurement periods yields a data set $U_{kpq}$ comprising the 16×4×4=256 ultrasonic signals.

Reconstruction algorithms permit synthetic off-line reconstruction of all physically possible focussings and coupling-in angles from these data and determining therefrom the transmission properties and reflection properties inside the test body 2 without requiring additional measurements.

Figure 2:
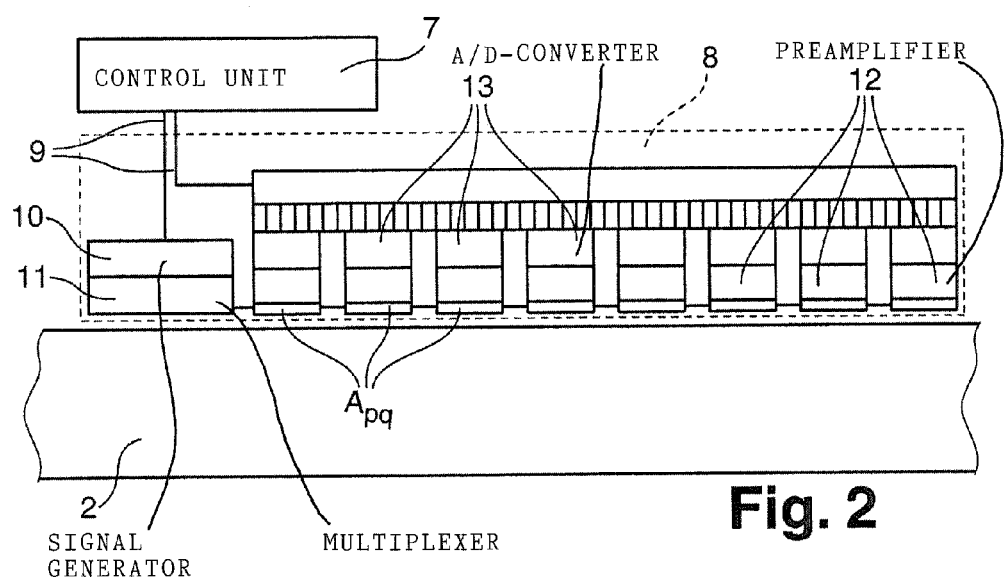
FIG. 2 shows a schematic set up for applying the method of the invention.

FIG. 2 shows an advantageous further embodiment of the method of the invention in association with devices. A control unit 7 and a probe 8 (broken-line edge) are provided with the data and control communication between control unit and the probe occurring in digital form via electrical lines 9. In this preferred embodiment, a signal generator 10, a multiplexer 11 and the electronics required for the A/D and D/A conversion are accommodated in the probe 8. The signal generator 10 generates a transmission impulse on a trigger signal of the control unit 7. The transmission impulse is conveyed via the multiplexer 11 to one or a multiplicity of ultrasonic transducers $A_{pq}$ in probe 8 and triggers it or them to couple ultrasonic waves into the test body 2. The ultrasonic signals received by the ultrasonic transducers $A_{pq}$ after reflection in test body 2 are first amplified by preamplifiers 12 in and A/D converter 13 provided for each ultrasonic transducer $A_{pq}$ and then digitalized. Then the digital data of the initially parallel individual ultrasonic transducers $A_{pq}$ are converted into serial form before they are transmitted via the data conduit 9 to the control unit 7 for storage.

LIST OF REFERENCES

1 array, ultrasonic transducer array
2 test body
3 surface, test body surface
4 imperfection
5 transmission path
6 reflection path
7 control unit
8 probe
9 electrical lines
10 signal generator
11 multiplexer
12 amplifier
13 A/D-converter

What is claimed is:

1. A method using ultrasound for non-destructive examination of a test body, whereby ultrasonic waves are coupled into the test body with at least one ultrasonic transducer and the ultrasonic waves are reflected inside the test body and are received by ultrasonic transducers and converted into ultrasonic signals, which form a basis for the non-destructive examination, comprising:
  a) providing n ultrasonic transducers on a surface of a test body with $n \geq 16$;
  b) selecting and activating a first ultrasonic transducer or a first group with i ultrasonic transducers from the n ultrasonic transducers for transmission of ultrasonic waves into the test body, with i<n;
  c) receiving the ultrasonic waves reflected inside the test body using m ultrasonic transducers, with $i < m \leq n$, and generating m ultrasonic signals;
  d) storing the m ultrasonic signals;
  e) selecting and activating another ultrasonic transducer or another group with i ultrasonic transducers, which differ from the first group by at least one ultrasonic transducer, for transmitting ultrasonic waves and carrying out process steps c) and d);
  f) repeating conducting of the process step e) with in each case selecting another ultrasonic transducer or another group of i ultrasonic transducers such that the other ultrasonic transducer or the other group with i ultrasonic transducers differs from an already selected ultrasonic transducer or from another already selected group with i ultrasonic transducers;
  g) evaluating the stored ultrasonic signals; and wherein
  h) providing of n ultrasonic transducers occurs in a two-dimensional array;
  i) activating all i ultrasonic transducers of a group occurs simultaneously, without phase shifting;
  j) evaluating the ultrasonic signals is carried out off-line using a reconstruction algorithm after conducting ultrasonic transmission through the test body;
  k) the reconstruction algorithm is selected based on at least one of a virtually preset coupling-in angle and a virtual focussing of the ultrasonic waves coupled into the test body and is applied to the stored ultrasonic signals; and
  l) receiving of the ultrasonic waves reflected inside the test body is conducted using all ultrasonic transducers provided on a surface of the test body, with m=n.

2. The method according to claim 1, wherein:
  when a first group with i transducers is selected for activation, activating all i ultrasonic transducers of a group occurs simultaneously, without phase shifting.

3. The method according to claim 1, wherein:
  when a first group with i transducers is selected for activation, activating of the i ultrasonic transducers of a group is carried out with each single ultrasonic transducer being activated with a different modulation so that the ultrasonic waves coupled into the test body are detected individually.

4. The method according to claim 1, wherein:
  when a first group with i transducers is selected for activation, selecting of the i ultrasonic transducers of a group is conducted so that adjacent ultrasonic transducers are selected according to one of a linear or planar array.

5. The method according to claim 1, wherein:
the ultrasonic transducers operate as one of electromagnetic and piezoelectric transducers.

6. The method according to claim 1, wherein:
evaluating the ultrasonic signals is carried out off-line using a reconstruction algorithm after conducting ultrasonic transmission through the test body; and
the reconstruction algorithm is selected based on at least one of a virtually preset coupling-in angle and a virtual focussing of the ultrasonic waves coupled into the test body and is applied to the stored ultrasonic signals.

7. The method according to claim 1, wherein:
generating and storage of the m ultrasonic signals utilizes analog/digital conversion in which the analog ultrasonic signals of the m ultrasonic transducers are converted into digital signals and stored in serial form.

8. The method according to claim 2, wherein:
when a first group with i transducers is selected for activation, selecting of the i ultrasonic transducers of a group is conducted so that directly adjacent ultrasonic transducers are selected according to one of a linear or planar array.

9. The method according to claim 3, wherein:
when a first group with i transducers is selected for activation, selecting of the i ultrasonic transducers of a group is conducted so that directly adjacent ultrasonic transducers are selected according to one of a linear or planar array.

10. The method according to claim 1, wherein:
generating and storage of the m ultrasonic signals utilizes analog/digital conversion in which the analog ultrasonic signals of the m ultrasonic transducers are converted into digital signals and stored in serial form.

* * * * *

UNITED STATES PATENT AND TRADEMARK OFFICE
CERTIFICATE OF CORRECTION

PATENT NO. : 8,365,600 B2  Page 1 of 1
APPLICATION NO. : 11/721235
DATED : February 5, 2013
INVENTOR(S) : Kröning et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1640 days.

Signed and Sealed this
First Day of September, 2015

Michelle K. Lee
*Director of the United States Patent and Trademark Office*